US006199318B1

(12) United States Patent
Stewart et al.

(10) Patent No.: US 6,199,318 B1
(45) Date of Patent: Mar. 13, 2001

(54) AQUEOUS EMULSIONS OF CRYSTALLINE POLYMERS FOR COATING SEEDS

(75) Inventors: Ray F. Stewart, Redwood City; Natarajan Balachander, Sunnyvale; Steven P. Bitler, Menlo Park; Loc Phan, San Jose; Valentine Y. Yoon, Santa Barbara, all of CA (US)

(73) Assignee: Landec Corporation, Menlo Park, CA (US)

( * ) Notice: Subject to any disclaimer, the term of this patent is extended or adjusted under 35 U.S.C. 154(b) by 0 days.

(21) Appl. No.: 08/929,750

(22) Filed: Sep. 15, 1997

Related U.S. Application Data (63) Continuation-in-part of application No. 08/766,865, filed on Dec. 12, 1996, now abandoned, and a continuation-in-part of application No. 08/769,639, filed on Dec. 12, 1996, now abandoned.

(51) Int. Cl.$^7$ ....................................................... A01C 1/04
(52) U.S. Cl. ............................. 47/57.6; 47/58.1; 524/156
(58) Field of Search ................................... 47/58.1, 57.6; 435/410; 524/156

(56) References Cited

U.S. PATENT DOCUMENTS

| | | |
|---|---|---|
| 3,644,241 | 2/1972 | Falivene . |
| 3,716,524 | 2/1973 | Canci . |
| 3,833,393 | 9/1974 | Kandathil . |
| 4,104,824 | 8/1978 | Lundberg et al. . |
| 4,184,020 | 1/1980 | Coupek et al. . |
| 4,196,190 | 4/1980 | Gehman et al. . |
| 4,401,688 | 8/1983 | Garnett et al. . |
| 4,439,946 | 4/1984 | Tobias . |
| 4,452,261 | 6/1984 | Bresak et al. . |
| 4,729,190 | 3/1988 | Lee . |
| 4,780,499 | 10/1988 | Villareal et al. . |
| 4,791,184 | 12/1988 | Nagai et al. . |
| 4,834,968 | 5/1989 | Bollch, Jr. . |
| 4,983,383 | 1/1991 | Makaimoski et al. . |
| 5,009,880 | 4/1991 | Grollier et al. . |
| 5,021,525 | 6/1991 | Montague et al. . |
| 5,025,062 | 6/1991 | Ley et al. . |
| 5,100,944 | 3/1992 | Walker et al. . |
| 5,104,642 | 4/1992 | Wells et al. . |
| 5,194,469 | 3/1993 | Srail et al. . |
| 5,225,480 | 7/1993 | Tseng et al. . |
| 5,284,907 | 2/1994 | Schulz et al. . |
| 5,314,530 | 5/1994 | Wierer et al. . |
| 5,318,995 | 6/1994 | Mondet et al. . |
| 5,324,762 | 6/1994 | Overend et al. . |
| 5,369,163 | 11/1994 | Chiou et al. . |
| 5,391,368 | 2/1995 | Gerstein . |
| 5,478,553 | 12/1995 | Chandran et al. . |
| 5,506,307 | 4/1996 | Memon . |
| 5,516,865 | 5/1996 | Urquiola . |
| 5,518,865 | 5/1996 | Urquiola . |
| 5,539,073 | 7/1996 | Taylor et al. . |
| 5,609,857 | 3/1997 | Chandran et al. . |
| 5,632,977 | 5/1997 | Chandran et al. . |
| 5,736,125 | 4/1998 | Morawsky et al. . |

FOREIGN PATENT DOCUMENTS

| | | |
|---|---|---|
| 6-192341 | 7/1994 | (JP) . |
| WO 92-10081 | 6/1992 | (WO) . |
| WO 93-21967 | 11/1993 | (WO) . |
| WO 96-27641 | 9/1996 | (WO) . |

OTHER PUBLICATIONS

Chemical Abstracts, vol. 103, No. 24, Dec. 16, 1985, Columbus Ohio, US; abstract No. 196567c, Hitachi Chemical Co Ltd.: "Granular Polymers," p. 11; XP002063723.

Chemical Abstracts, vol. 112, No. 20, May 14, 1990, Columbus Ohio, US; abstract No. 180099b, Tayama S. et al: "Method for suspension polymerization," p. 15 XP000063301.

Chemical Abstracts, vol. 119, No. 24, Dec. 13, 1993, Columbus Ohio, US; abstract No. 250751d, Imamura Takeshi et al.: "Preparation of polymer particles with narrow particle size by suspension polymerization," p. 19; XP000407439.

C. E. Rehberg et al., *Preparation and Properties of the n–Alkyl Acrylates*, vol. 66, Jul. 1944, pp. 1203–1207.

U. S. Satpathy et al., *Emulsion Polymerisation of Highly Water–Insoluble Monomers*, British Polymer Journal, vol. 20, No. 6 (1988), pp. 521–524.

*Anti–Static Agents*, Kirk–Othmer, *Encyclopedia of Chemical Technology*, 4th Ed., vol. 3, pp. 552–564, John Wiley & Sons.

*Bleaching Agents*, Kirk–Othmer, *Encyclopedia of Chemical Technology*, 4th Ed., vol. 4, pp. 271–296, John Wiley & Sons.

*Hair Preparations*, Kirk–Othmer, *Encyclopedia of Chemical Technology*, 4th Ed., vol. 12, pp. 881–917, John Wiley & Sons.

*Primary Examiner*—Leon B. Lankford, Jr.
(74) *Attorney, Agent, or Firm*—Sheldon & Mak (57) ABSTRACT

Crystalline polymers are prepared as a latex, and are useful for coating fibrous materials such hair and fabrics. The latex can have a high solids content greater than 30%, a residual monomer content of less than 1%, and can be used for repeatedly setting fibrous materials into desired configurations. The latex is also useful for coating organisms such as seeds. The particulate coating extends the dormancy of the organism and/or protects the organism, and is easily shed by a germinating seed. The coating can contain a seed coating additive, such as a colorant or fungicide.

36 Claims, 1 Drawing Sheet

FIG.

AQUEOUS EMULSIONS OF CRYSTALLINE POLYMERS FOR COATING SEEDS

CROSS-REFERENCE

This application is a continuation-in-part of application Ser. No. 08/766,865 filed on Dec. 12, 1996 now abandoned, entitled "PROTECTIVE COATINGS FOR ORGANISMS," the disclosure of which is incorporated herein by reference, and is related to application Ser. No. 08/769,639 filed on Dec. 12, 1996, now abandoned entitled "AQUEOUS EMULSIONS OF CRYSTALLINE POLYMERS AND USE THEREOF FOR SHAPE-SETTING FLEXIBLE MATERIALS" by Stewart et al., now abandoned in favor of continuation-in-part application Ser. No. 09/210,421.

BACKGROUND

This invention relates to protective coatings for controlling the germination of seeds.

One of the most critical periods for plant emergence is the period between seed planting and germination. After planting, seeds usually must take in water before germination can start. This process is called imbibition. Most seeds initiate imbibition irrespective of the temperature of the soil. Once imbibition starts, however, germination must occur within a short period of time.

In contrast, ideal germination occurs only after the soil temperature increases to reach a critical soil temperature. If imbibition occurs long before the critical soil temperature is achieved, the seed can become diseased or die from chilling injury and crop yields are correspondingly lower. For example, dry seeds such as dry soy bean seeds typically contain about 7% to 14% by weight of moisture in their dormant state. If the seed imbibes substantial amounts of water above 14% at temperatures below the critical soil temperature, the seed is likely to suffer injury.

Thus, it is advantageous to control seed water uptake so that imbibition occurs only when the soil temperature is in the temperature range that promotes ideal germination for the end result that crop yields will be enhanced.

One of the inventors for the present invention, Ray F. Stewart, previously invented temperature-sensitive seed germination control as described in U.S. Pat. No. 5,129,180, which is incorporated herein by reference. In this invention, various types of coated organisms, such as coated seeds, were provided with a coating comprised of a polymeric material which has a temperature-dependent permeability. Preferred polymeric materials were side-chain crystallizable polymers. The polymer coating, when applied to a seed, prevents germination of the seed due to lack of water. The coating is permeable to water at a temperature above a transition temperature of the polymers for allowing germination of the seed.

A difficulty with the coatings described in U.S. Pat. No. 5,129,180 is that the coating systems are organic solvent based. There is concern that organic solvents can adversely affect the seeds, and any residual solvent left in the coatings can adversely affect plant growth and be deleterious to soil. Moreover, difficulties in the seed shedding the coating when temperatures are sufficiently high for seeds to germinate and grow have been noted, whereby the non-shed coating inhibits seed germination and plant growth.

Another problem noted with preexisting coatings is cracking at low temperatures due to the brittleness of the coating. Under these circumstances, water can prematurely be imbibed by the coated seed, resulting in premature germination and resultant stunted growth or death of the plant.

Accordingly, there is a need for a coating system for seeds and other organisms that is substantially solvent-free, and the formed coating does not crack at low temperatures and the coating is easily shed by the seed at temperatures conducive to ideal germination and growth.

SUMMARY

The present invention satisfies these needs with (i) novel, aqueous, non-phytotoxic compositions suitable for use in coating seeds, the compositions comprising crystalline polymeric particles suspended in water; (ii) use of the compositions for coating organisms; and (iii) coated organisms. The particles comprise a crystalline polymer having a melting temperature greater than 0° C. and less than about 40° C. A particulate coating is formed on an organism by applying the composition to the organism and having the water evaporate from the composition, either at ambient conditions or by application of heat. The composition contains sufficient particles that the particulate coating is impermeable to water at a temperature below the melting temperature, $T_m$, of the crystalline polymer for extending the dormancy of the organism due to lack of water at temperatures below $T_m$. The water permeability of the coating is at least three times more above $T_m$ as compared to the water permeability below $T_m$ so that the organism can become non-dormant above the Tm.

Preferably the particles comprise the crosslinked polymeric reaction product of a monomer component comprising (i) a hydrophobic monomer component, (ii) a hydrophilic monomer component, and (iii) a sufficient amount of at least one crosslinking monomer having at least two polymerizable groups that the polymeric reaction product has a gel content of at least 50%.

The hydrophobic monomer component comprises a first hydrophobic monomer such that a homopolymer thereof is crystallizable. Preferably the hydrophobic monomer component includes a second hydrophobic monomer having a glass transition temperature $T_g$, wherein a homopolymer of the second hydrophobic monomer is amorphous. Preferably the monomer component contains a sufficient amount of the second hydrophobic monomer that a coating formed has a tack at ($T_m$+10° C.) less than 50% of the tack at ($T_m$+10° C.) of a coating formed without the second hydrophobic monomer.

The hydrophilic monomer component comprises one or more hydrophilic monomers, and is present in an amount of at least 2% and up to about 10% by weight based on the weight of the monomer component. Typically the weight ratio of the hydrophobic monomer component to the hydrophilic monomer component is from about 10:1 to about 50:1. The weight ratio of the hydrophobic monomer component to the hydrophilic monomer component is sufficiently large that the polymeric reaction product is crystalline. The coating composition contains sufficient surfactant to suspend the particles in the water.

Preferably the monomer content of the coating composition is less than 1% by weight based on the weight of the particles, i.e., there is substantially no residual monomer.

When coating corn, preferably the composition contains a fluorosurfactant.

Preferably the coating contains at least one seed coating additive, such as a colorant, filler, soil pH adjustor, phytotoxicity inhibitor, fungicide, herbicide, and/or insecticide. Colorant can be included in the coating so that it is easy to distinguish coated seeds from non-coated seeds.

It has been determined that the combination of the internal crosslinking of the particles, and the inclusion of the second hydrophobic monomer, results in a coating that maintains its integrity at low temperatures, and is easily removed from the seed at temperatures greater than $T_m$. It has been learned that without the crosslinking, there is great difficulty in removing the coating from the seeds at temperatures greater than $T_m$. Furthermore, we learned that without the second hydrophobic monomer, it is difficult to apply the coating, in that the coating is tacky at temperatures greater than $T_m$ that are typically required for applying the seed coating, and tends to form poor quality films.

The composition is prepared by an aqueous polymerization process. An aqueous reaction medium is provided, the medium comprising water, the monomer, the surfactant component, and a cosolvent. At least 99% by weight of the monomer component is polymerized to form the crystalline copolymer as latex particles of a latex, the particles having an average particle size of less than 0.5 microns. Typically, the cosolvent is then removed from the latex. Preferably, the aqueous reaction medium contains sufficient monomer component that the latex has a solids content of at least 30%.

The aqueous medium contains sufficient surfactant and sufficient cosolvent that the second hydrophobic monomer component is substantially randomly dispersed in the crystalline polymer. The more cosolvent used in the aqueous reaction medium, the less surfactant required. Preferably the surfactant component comprises at least one ionic surfactant having a hydrophilic lipophilic balance of from about 20 to about 40, and at least one non-ionic surfactant having a hydrophilic lipophilic balance of from about 5 to about 30. Typically the aqueous reaction medium contains the surfactant in an amount of about 0.8 to about 10% by weight, based on the weight of the monomer component.

As discussed, the crosslinking monomers render the coating formed from the latex more easily removable and prevent the particles of the coating from sticking together, thereby avoiding the problem of seed germination and plant growth being stunted by the coating. Another technique for rendering a coating made from the latex composition easily removable is to include in the aqueous reaction medium one or more monomers containing free carboxyl groups, and neutralizing at least 25% of the carboxyl groups with a nonvolatile neutralizing agent such as sodium bicarbonate.

The present invention provides a water-based crystalline polymer composition useful for coating organisms, where the composition has high solids content, low residual monomer content, and can be economically prepared in commercial quantities. Moreover, when applied to organisms, the resultant coating is durable, and can be made easily removable.

There are additional advantages of the present invention. For example, coated seeds can be planted early in the planting season and not undergo imbibition even under moist soil conditions unless temperature conditions are favorable. The polymeric coating material undergoes a temperature-dependent phase change which dramatically changes the water permeability of the material. Due to the impermeability of the coating with respect to water at lower temperatures, the seed does not take on water at lower temperatures and be subjected to diseases caused by fungi or other pathogens.

Another advantage of the present invention is that it provides for greater flexibility and efficiency with respect to the timing of seed planting. There is greater flexibility in the use of the labor force due to an expanded planting period without substantial risk of a need for replanting due to chilling injury at undesirable low temperatures. The coated seeds of the invention allow early planting of the seeds so that the grower is better able to utilize manpower resources and reduce scheduling conflicts with respect to manpower and equipment.

Another advantage of the present invention is an increase in the yield of early planted food and fiber crops due to optimum germination control. There is a reduction in water-stress damage to seeds resulting in a more vigorous, disease and pest resistant planting. Further, there is reduced seed loss due to cool, damp conditions.

An important feature of the invention is that the coating provides for the elimination and/or reduction of fungal attack to ungerminated seeds and thus a reduction in the need for fungicides, thus reducing costs and providing an environmental benefit.

Another advantage of the invention is germination timing is controlled by providing coated seeds which produce crops which mature in a more uniform manner (with respect to factors such as crop height) as compared to crops from uncoated seeds, thus allowing a larger percentage of the crop to be harvested at the same time.

Another advantage of the invention is that the coating with temperature-sensitive permeability can be used in combination with other like and different coatings alone or in combination with other materials such as fertilizers, insecticides, fungicides, plant growth regulators, herbicides and the like which enhance growth and/or protect the organism against harmful diseases and/or elements.

DRAWINGS

These and other features, aspects and advantages of the present invention will become better understood with reference to the following description, appended claims, and accompanying drawings, where:

The FIGURE is a schematic view of a seed coated with a particulate coating prepared according to the present invention.

Figure 1:
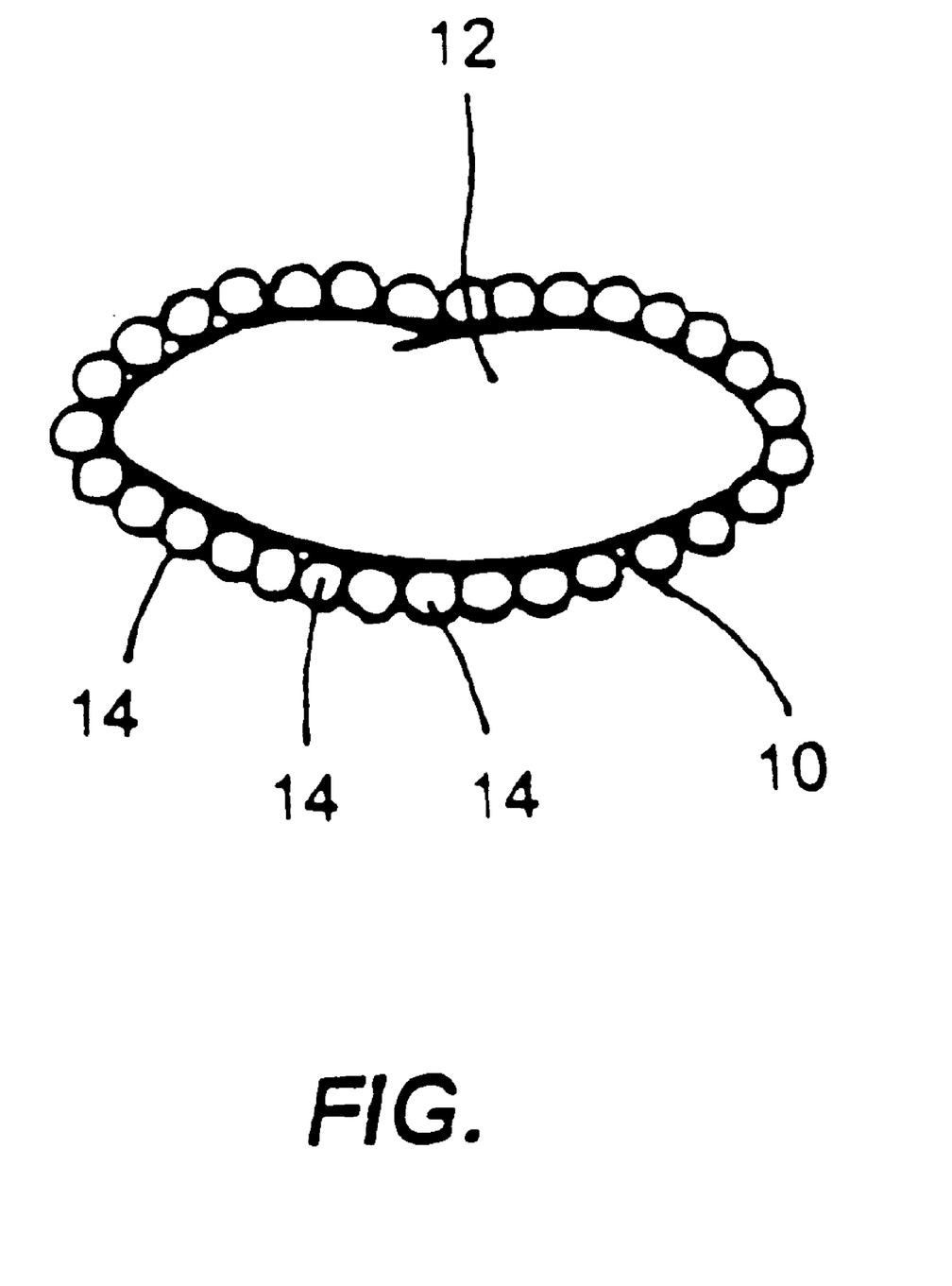

Coatings for seeds comprise a latex of a crystalline polymer and a seed-coating additive. The latex is prepared by providing an aqueous reaction medium or mixture comprising a monomer component and polymerizing the monomer component in an aqueous emulsion polymerization reaction.

Reaction Medium

The monomer component of the reaction medium includes a hydrophobic monomer component comprising one or more hydrophobic monomers and a hydrophilic monomer component. The term "hydrophobic monomer" refers to a monomer having solubility in water of less than 2% by weight at 25° C. The term "hydrophilic monomer" refers to a monomer having a solubility in water greater than 2% by weight at 25° C.

The reaction medium comprises, in addition to water and the hydrophobic monomer component, a hydrophilic monomer component comprising one or more hydrophilic monomers, a surfactant component preferably comprising at least one ionic surfactant and at least one nonionic surfactant, and optionally, a cosolvent to increase water solubility of the hydrophobic monomers.

Monomer incorporation into the forming polymer is controlled by altering the diffusion rate of the monomers into the growing latex particles by including in the reaction medium the surfactant component and, optionally, by one or more cosolvents.

Hydrophobic Monomer Component

The hydrophobic monomers typically are alpha, beta ethylenically unsaturated monomers, preferably n-alkyl (meth)acrylates whose carbon chain is from about 4 to about 24 carbons long. Generally the hydrophobic monomer component comprises a (i) first hydrophobic monomer, a homopolymer of which is a crystalline polymer, and (ii) a second hydrophobic monomer, a homopolymer of which is amorphous, used as a modifier to modify properties such as the melting temperature of the resultant polymer, and the tack of a coating formed from the polymer. The term "crystalline monomer" is used to refer to a monomer whose homopolymer is a crystalline polymer. The term "amorphous monomer" is used to refer to a monomer whose homopolymer is amorphous.

Preferably the first hydrophobic monomer is one whose homopolymer is an SCC polymer. Preferably there is a sufficient amount of the first monomer component, that the resultant product prepared is an SCC polymer. SCC polymers are crystalline polymers having a crystalline melting point which is determined by the melting point of long chain crystalline side chains attached to a polymer backbone. They are well known, and are described for example in J. Poly. Sci. 60, 19 (1962), J. Poly. Sci. (Polymer Chemistry) 7, 3053 (1969), 9, 1835, 3349, 3351, 3367, 10, 1657, 3347, 18, 2197, 19, 1871, J. Poly. Sci., Poly Physics Ed 18 2197 (1980), J. Poly. Sci. Macromol. Rev. 8, 117 (1974), Macromolecules 12, 94 (1979), 13, 12, 15, 18, 2141, 19, 611, JACS 75, 3326 (1953), 76, 6280, Polymer J 17, 991 (1985), Poly. Sci USSR 21, 241 (1979), U.S. Pat. Nos. 4,380,855, 5,120,349, 5,129,180, 5,156,411, 5,254,354, 5,387,450 and 5,412,035, and copending commonly assigned U.S. patent application Ser. No. 08/048,280 filed Apr. 14, 1993, now U.S. Pat. No. 5,665,822, and the corresponding published International patent application Nos. PCT/US92/08508 and PCT/US94/04138. The disclosure of each of these publications, patents, and patent applications is incorporated herein by reference for all purposes.

SCC polymers can have sharp melting points. Thus, an SCC polymer has an onset-of-melting temperature, $T_o$, which is below, but not very far below, the peak crystalline melting temperature, $T_p$, generally less than 20° C. below, preferably less than 15° C. below $T_p$. The $T_o$ and $T_p$ values as used herein are measured on a Differential Scanning Calorimeter ("DSC") at a heating rate of 10° C. per minute and using the second heat cycle. The $T_p$, and preferably also the $T_o$, of the SCC polymers are preferably −10 to 90° C., particularly 0 to 80° C. Preferably $T_p-T_o$ is less than 10° C. The "melting point," $T_m$ of the polymers as described herein is taken as the endotherm peak temperature when measured at a rate of 10° C./min, is between $T_o$ and $T_p$, and is also referred to as the "phase transition temperature."

The SCC polymers comprise repeating units of the general formula where Y is an organic radical forming part of the polymer backbone and Cy comprises a crystalline moiety. The crystalline moiety may be connected to the polymer backbone directly or through a divalent organic or inorganic radical, e.g. an ester, carbonyl, amide, hydrocarbon (for example phenylene), amino, or ether link, or through an ionic salt linkage (for example a carboxyalkyl ammonium, sulfonium or phosphonium ion pair). The radical Cy may be aliphatic or aromatic, for example alkyl of at least 10 carbons, fluoroalkyl of at least 6 carbons or p-alkyl styrene wherein the alkyl contains 6 to 24 carbons. The SCC polymer may contain two or more different repeating units of this general formula.

Preferred first hydrophobic monomers for preparing SCC polymers are monomers with side chains containing in total at least 5 times as many carbon atoms as the backbone of the monomer, particularly side chains comprising linear polymethylene moieties containing 12 to 50, especially 14 to 22, carbon atoms, or linear perfluorinated or substantially perfluorinated polymethylene moieties containing 6 to 50 carbon atoms. Other preferred first hydrophobic monomers include vinyl esters of carboxylic acids where the carboxylic acid group contains between 6 to 20 carbons. Polymers containing such side chains can be prepared by polymerizing one or more corresponding linear aliphatic acrylates or methacrylates, or equivalent monomers such as acrylamides or methacrylamides. A number of such monomers are available commercially, either as individual monomers or as mixtures of identified monomers, for example C12A, C14A, C16A, C18A, C22A, a mixture of C18A, C20A and C22A, a mixture of C26A to C40A, fluorinated C8A (AE800 from American Hoechst) and a mixture of fluorinated C8A, C10A and C12A (AE12 from American Hoechst).

In a preferred embodiment the hydrophobic crystalline monomer is selected from the group consisting of dodecyl acrylate, hexadecyl (meth)acrylate, tetradecyl (meth)acrylate, octadecyl (meth)acrylate, dodocosyl (meth)acrylate, and mixtures thereof.

The second hydrophobic monomer is a monomer which can form an amorphous homopolymer with a glass transition temperature $T_g$ which is above or below the melting temperature $T_m$ of the first monomer. When $T_g$ is below $T_m$, inclusion of the second monomer decreases the brittleness of the polymer coating that can be formed from the latex and reduces cracking at temperatures below $T_m$. This is an important advantage of the present invention, in that sloughing off of the coating due to premature imbibition of water is due to low temperature cracking. When $T_g$ is above $T_m$, the tack of the polymer coating is reduced. The second hydrophobic monomers are preferably selected from hydrophobic amorphous monomers such as linear or branched alkyl, hydroxyalkyl and alkoxyalkyl acrylates, methacrylates, acrylamides and methacrylamides; and vinyl esters. Preferred monomers are dodecyl methacrylates, decyl (meth)acrylates, octyl (meth)acrylates including iso-octyl (meth)acrylate and 2-ethyl-hexyl (meth)acrylate, hexyl (meth)acrylates, butyl (meth)acrylates, or a mixture of these monomers. The second hydrophobic monomer preferably is selected from the group consisting of octyl (meth)acrylate, hexyl (meth)acrylate, butyl (meth)acrylate, and mixtures thereof.

$T_g$ of the second hydrophobic monomer is typically from about −50 to about 120° C. The $T_g$'s for several exemplary homopolymers resulting from polymerization of the corresponding second hydrophobic monomer are:
poly(n-butyl methacrylate): 32° C.,
poly(isobutylmethacrylate): 65° C.,
poly(t-butylmethacrylate): 107° C.,
poly(vinyl acetate): 28° C.,
poly(vinyl propionate): 10° C.,
poly(t-butyl acrylate): 40° C., and
poly(n-butyl acrylate): 52° C.

When $T_g$ is less than $T_m$, preferably the reaction medium contains a sufficient amount of the second hydrophobic monomer that the formed crystalline polymer has a melting temperature at least 5° C. less than $T_m$. Where $T_g$ is greater than $T_m$, preferably there is sufficient second hydrophobic monomer in the reaction medium that the coating formed from the latex has a tack at ($T_m$+10° C.) of less than 60%, and preferably less than 50%, of the tack at ($T_m$+10° C.) of a coating formed from the same latex without the second hydrophobic monomer.

As used herein, tack refers to self tack and is measured by the peel method now described. A quantity of latex is applied onto a suitable backing film such as polyester available for example from Dupont under the tradename Mylar or a filled polyolefin film available from PPG under the tradename Teslin. The latex is applied at a uniform thickness (e.g., 30 microns dry film thickness) using a wire wound rod or other suitable means. The coated film is dried at 65° C. for 2 hours and then allowed to equilibrate at room temperature for 24 hours. Two such films are then laminated together at 35° C. and peeled apart with a slip/peel tester (manufactured by IMS) at a rate of 230 cm/min.

Hydrophilic Monomer Component

Preferably, the hydrophilic monomer component comprises one or more alpha, beta ethylenically unsaturated monomers. More preferably, the hydrophilic monomers are vinylic compounds such as acrylic acid, methacrylic acid, other alkyl, hydroxyalkyl and alkoxyalkyl acrylates and methacrylates (e.g. hydroxy ethyl methacrylate), acrylamides and methacrylamides; acrylic and methacrylic acids; acrylamide; methacrylamide; maleic anhydride; itaconic acid; comonomers containing amine groups; and 2-acrylamido-2-methylpropane sulfonic acid (AMPS) and combinations thereof.

Preferably the hydrophilic monomer is selected from the group consisting of acrylic acid, methacrylic acid, itaconic acid or 2-acrylamido-2-methylpropane sulfonic acid, acrylamide, methacrylamide, hydroxyethyl (meth)acrylate and mixtures thereof.

Crosslinking Monomers

The monomer component preferably includes one or more crosslinking monomers, which can be either a hydrophobic or hydrophilic monomer. The crosslinking monomers internally crosslink the particles of the latex by increasing the chain extension and molecular weight, thereby stabilizing the polymer particles, adjusting the film forming properties of the resultant latex, and controlling the tack level of the resulting polymer, especially above the melting point of the polymer. For example, by adding a sufficient amount of crosslinking monomer to the reaction medium, the gel content of the resultant polymer can be raised to 50% by weight or more, such as at least 60%, and as much as 100% by weight, which renders particulate coatings formed from the latex product more easily removable and frangible.

This is an important feature for seed coatings because prior art non-particulate coatings have remained on the seed and inhibited seed germination. When a polymer latex is internally crosslinked each of the individual polymer particles are crosslinked internally creating harder particles. When this sort of polymer latex is coated on a seed, the hard particles do not easily diffuse into neighboring particles and an unstable film is formed. This is advantageous in that such a coating will fall apart faster than one without internal crosslinks when a seed starts to expand. Generally, when a coating formulation is deposited on the seed and the water evaporated, the individual latex particles are brought together by capillary action, and the water is squeezed out from the interstitial spaces. The individual polymer particles are brought together and film formation occurs. After film formation, individual particles flow together causing particle coalescence. After particle coalescence it is much harder for the polymer coating to fall apart when a seed is expanding during water imbibition. Internal crosslinking avoids this problem.

These crosslinking monomers are monomers that generally have two or more polymerizable groups, such as vinylic groups. Preferred hydrophobic crosslinking monomers include 1,4-butanediol diacrylate, 1,6-hexanediol diacrylate, 1,14-tetradecyldiol diacrylate, divinyl benzene, vinyl crotonate, divinyl ether, 1,3,5-triallyl triazine trione, and mixtures thereof. Suitable hydrophilic crosslinking monomers include ethylene glycol diacrylate, ethylene glycol dimethacrylate, and mixtures thereof.

Quantity of Monomers

The monomer component comprises, based on the weight of the monomer component, at least 90% by weight of the hydrophobic monomers. The hydrophilic monomer component, when present, comprises from about 2 to about 10%, and more typically from about 2 to 5% by weight of the total weight of the monomer component. Typically, the weight ratio of the hydrophobic monomer component to the hydrophilic component is from about 10:1 to about 50:1. The weight ratio of the first monomer to the second monomer is at least 1:1. Typically, the second hydrophobic monomer is present in an amount of about 5 to about 40%, and more typically from about 5% to about 30% by weight of the weight of the hydrophobic monomer component.

The crosslinking monomer, whether a hydrophilic or hydrophobic crosslinking monomer, typically is present in a quantity of from about 0.1 to 10% by weight, preferably from about 0.5 to about 5% by weight of the monomer component. Sufficient crosslinking monomer is used that the crystalline polymer has a gel content of at least 50%, preferably at least 60%, and as much as 100% by weight.

Preferably sufficient monomer component is included in the reaction medium that upon polymerization of the monomer, the resultant product has a solids content of greater than 25%, more preferably at least 30%, and most preferably greater than 35%. In general, the higher the solids content, the less water that needs to be evaporated from the resultant latex to form a coating, and the more energy efficient the product. Also, the higher the solids contents, the less expensive it is to package and transport sufficient latex for coating a product. However, generally the solids content is no more than 45%, because of the tendency for very high solids latices to become unstable and coagulate spontaneously.

Surfactants

The reaction medium contains sufficient surfactant to suspend and stabilize in water the particles formed by polymerizing the monomer component. The surfactant component typically consists of mixtures of anionic and nonionic surfactants. Such mixtures can include polymerizable surfactants. A single anionic surfactant or a mixture of two or more anionic surfactants can be employed. More than one nonionic surfactant can also be used. Typically these surfactants are added in the range of from about 0.8 to about 10% by weight, preferably from about 1 to about 5%, based on total reaction components. Preferably the reaction medium contains sufficient surfactant that the monomer component is dispersed in the reaction medium as droplets having a diameter greater than about 10 microns.

Surfactants are characterized by a hydrophile-lipophile balance (HLB) number that describes the strength of the hydrophilicity to the lipophilicity of the surfactant. Anionic surfactants having a HLB number of about 20 to 40 are typically employed in the polymerization reaction mixtures. These surfactants function to form micelles at low concentrations and to act as nucleation sites for the latex particles. Once nucleation is complete, the surfactants can additionally provide charge stabilization to the growing latex particles. Preferably the anionic surfactants contain a sulfate or sulfonate group and a hydrophobic moiety and may be, for example, alkyl sulfates, alkyl ether sulfonates and sulfates, alkylaryl sulfonates, and sulfosuccinates. Preferred anionic surfactants are the amine salt of dodecyl benzene sulfonic acid, a salt of dioctyl sulfosuccinate, a salt of lauryl sulfate or a salt of the ethoxylated alcohol half ester of sulfosuccinic acid. Exemplary alkyl and alkene sulfonates are described in U.S. Pat. Nos. 4,983,383 and 5,194,469 which are herein incorporated by reference.

Nonionic surfactants having HLB number of about 5 to about 35, preferably between about 10 and 15, can also be employed. The primary purpose of these surfactants is to lower the interfacial tension between the monomer oil droplets and the aqueous phase and to provide stabilization of the polymer dispersion by partitioning at the interface of the aqueous phase and the polymer particles. In this manner, nonionic surfactants are added to reduce the polymer dispersion's sensitivity to factors such as shear, temperature and the presence of electrolytes.

The nonionic surfactants can be linear or branched ethoxylated alcohols, ethoxylated alkylphenols and block copolymers of ethylene oxide and propylene oxide. Preferably the nonionic surfactants contain between about 3 to 40 ethylene oxide repeat units and a hydrophobic moiety which may be linear or branched $C_{11}$–$C_{15}$ secondary alcohols, nonylphenol or octylphenol, or block copolymers of ethylene oxide and propylene oxide.

Cosolvents

Cosolvents, also referred to as diffusion modifiers, can be included in the reaction mixture in an amount up to about 30% by weight based on the water content, and preferably in an amount of from about 5 to about 20% by weight. Cosolvents increase the water solubility of the hydrophobic monomers, thereby increasing the transport rate of the hydrophobic monomer component from the monomer micelles or oil droplets to polymer nucleation sites. The cosolvents are selected from linear or branched C1 to C4 monoalkanols and C3 to C6 alkyl esters and alkyl ethers. Preferred cosolvents are those that have a solubility in water that is greater than that of n-butyl acetate (0.7% at 25° C.). The cosolvents typically have boiling points in the range from about 60° to 130° C., and preferably less than 95° C., so that the cosolvents can easily be removed after the polymerization reaction by evaporation. Preferred cosolvents are selected from the group consisting of ethanol, isopropanol, ethyl acetate, n-propanol, sec-butanol, t-butanol, and combinations thereof. Preferably the cosolvent has a water-octanol partition coefficient of at least about 0.2 to enhance the solubility of the hydrophobic monomers in the water.

Exemplary octanol/water partition coefficients, $K_{ow}$, are:
methanol (estimate): 0.1
ethanol: 0.49
2-propanol: 1.12
2-butanol (estimate): 2.5
ethylacetate (estimate): 5
These values are obtained or estimated from "Handbook of Property Estimation Methods," edited by W. J. Lyman, W. F. Reehl, D. H. Rosenblatt, American Chemical Society, Washington, D.C. 1990.

The amount of cosolvent used depends upon the amount and type of surfactant used. For example, where the emulsion polymerization reaction occurs in the presence of about 1.6% by weight of ionic and non-ionic surfactants combined, at least 5% of the cosolvent is generally required to obtain a single sharp melting point crystalline polymer. When the reaction is performed in the presence of only about 0.8% by weight of ionic and non-ionic surfactants combined, at least about 10% of the cosolvent is generally required.

Polymerization Reaction

The reaction medium is emulsified in a vessel using conventional equipment, such as stirrers. After emulsification, the polymerization reaction is initiated by adding at least one source of free radicals as initiators. The free radical source is normally employed at a concentration within the range of 0.1 to 0.4% by weight. The free radical generator can be a hydrophilic or hydrophobic compound. Examples of hydrophilic free radical generators include potassium persulfate, ammonium persulfate and hydrogen peroxide. Examples of hydrophobic free radical generators include benzoyl peroxide and di-t-butyl peroxide. The polymerization reaction can also employ a redox initiator, such as t-butyl hydroperoxide/ascorbic acid or hydrogen peroxide with a ferrous compound. Alternatively, UV radiation can be employed to produce the radicals.

Initiators useful in emulsion polymerization processes are known to those skilled in the art and are described in "Emulsion Polymerization," D. C. Blackley, 1975, Chapter 6, Applied Science Publishers, Ltd., London. Suitable initiators are also described in U.S. Pat. No. 5,516,865.

The emulsion polymerization reactions are typically carried out at temperatures ranging from about 45° to about 90° C., preferably from about 60° to about 80° C. Lower temperatures decrease the amount of coagulum observed in the reactions and increase the particle size uniformity of the dispersion. Under all polymerization conditions tested, the amount of coagulum is less than 1% and the particle size less than 0.5 microns. The reaction preferably occurs in an oxygen free atmosphere such as under a nitrogen blanket.

The pH of the reaction mixture is maintained from about 2 to about 9 by adding, as necessary, pH adjusters and buffers to the reaction mixture. Useful pH buffers include sodium bicarbonate, sodium hydrogen phosphate, and the like. Useful adjusters include sodium hydroxide and ammonium hydroxide.

Preferably the reaction takes place until 99% of the monomer is polymerized, i.e., the final product has a residual monomer content of less than 1%. This typically takes from about 1 to about 4 hours at a temperature of about 70° C. After polymerization, the cosolvent can be removed by evaporation.

The resulting latex is stable, and has many applications, as described below. The resulting latex has a residual monomer content of less than 1% by weight based on the weight of the particles.

If desired, additives can be included, such as additional pH adjusters, additional pH buffers, coalescing agents, colloidal stabilizers, rheology modifiers, and defoamers. Coalescing agents can be admixed with the latex in order to ensure adequate coverage of a coating on a substrate. Useful coalescing agents include, but are not limited to N-methylpyrrolidone, Carbitol (trademark) series of poly (ethylene glycol) alkyl ethers (available from Union Carbide), and mixtures thereof. Poly(ethylene glycol) at different molecular weights can also be added. Examples of colloidal stabilizers are hydroxyethyl cellulose, polyacrylates and polyvinyl alcohols sold under the trade names Mowiol (Celanese) and Elvanol (Dupont), respectively. Rheology modifiers can be added to improve the rheological properties of the latex. Useful rheology modifiers include, but are not limited to Kelzan (trademark) series available from Kelco, hydroxyethyl cellulose, UCAR (trademark) Polyphobe series (available from Union Carbide), and mixtures thereof. Defoamers can be added in applications in which foam is generated. Useful defoamers include, but are not limited to, Surfynol (trademark) series (available from Air Products), Anti-foam H-10 Emulsion (available from Dow Corning), and mixtures thereof.

A particularly useful surfactant or wetting agent for coating corn is a fluorosurfactant such as LODYNE S-106A available from Ciba-Geigy.

External Crosslinks

In some applications it is desirable to include one or more external crosslinkers. External crosslinkers typically act by bridging two or more particles increasing the apparent molecular weight of the polymer and increasing the mechanical strength of the film. Generally, the external crosslinkers are charged compounds that interact with charged groups in the polymer latex, typically a metal cation or a bi- or multidentate amine. These charged compounds include metal cations selected from the group consisting of magnesium, manganese, zinc, calcium, titanium, and zirconium cations, and is preferably $Zn^{++}$. Non-metallic and organic crosslinkers can also be used. These include triethylene tetramine, ethylene diamine, diethyl aminopropylamine, and bis quarternary ammonium salts (bisquats). These agents are added to the polymer to form crosslink sites are present in the range of about 0.1 to 10% by weight, preferably 0.5 to 3. External crosslinkers may first be added to a polymer latex in a noncrosslinking state which is then activated to a crosslinkable state once a coating is formed with the polymer latex. For example, Zinplex 15, which is an aqueous solution of zinc containing the $Zn(NH_3)^{++}$ ions available from Rohm and Haas, complexes carboxyl groups only after the ammonia in the complex is removed by evaporation.

Generally, the crosslink density of a polymer is described as the number of crosslinks per weight average molecular weight. For example, a polymer having an average molecular weight of 125,000 and having an average of 1 intermolecular crosslink per polymer chain is stated to have a crosslink density of 1. In order for a crystalline polymer to resist flow above the melt, it is desirable to have a crosslink density greater than about 0.01, preferably greater than 0.05, and most preferably greater than 0.1. It is not necessary for all of the polymer chains in a material to be crosslinked and a high gel content is not generally necessary unless the application requires great solvent resistance. Generally crosslinking beyond about 1 to 10 mole percent is not necessary under normal circumstances and excessive crosslinking can result in decreased crystallinity and impaired performance. The optimal crosslink density for a given polymer will depend to a large extent on the molecular structure and repeat unit size, larger repeat unit size matching generally well with generally increased crosslinking density. The crosslinked polymers normally have a heat of fusion of at least about 10 Joules/g, more usually at least 20 Joules/g.

It is also desirable to use a combination of internal and external crosslinkers. In this case, the tendency of internal crosslinkers to form a coating that fall apart easily once the seed starts expanding is balanced against the tendency of external crosslinkers to form a coating with greater mechanical strength. Thus, when external crosslinkers are used with internally crosslinked latex polymers, they tend to decrease the ease with which the polymer latex coating falls apart when the seed starts to expand, and to give some mechanical strength to the coating.

For seed coating applications, the crystalline polymers are chosen and formulated so that they: (1) can form seed coatings which retain their shape and structure and do not freely flow below a given temperature range which temperature is generally too cool for optimum germination; (2) exhibit one or more phase transitions at phase transition temperature points; (3) have substantially greater permeability to water at temperatures equal to or greater than a selected temperature than at temperatures below the selected temperature; and (4) are structurally positioned so as to regulate the flow of a material such as water between an outside environment and the seed whereby water flow between the outside environment and the seed is regulated by changing the temperature and thereby changing the permeability of the material with respect to water and thus controlling the timing of the germination of the seed.

Regarding feature (1) above, the polymer may be combined with other polymers to aid structural integrity. With respect to features (2) and (3) the phase change preferably takes place in the range of 5° C. to 40° C., more preferably 18° C. to 30° C. at which temperature the permeability increases twofold, preferably threefold or more as compared to the permeability below the phase transition temperature.

Preferred Polymers

Crystalline polymers according to the present invention have a sharp melting point, in that the difference between $T_o$ and $T_p$ is less than 20° C., and preferably less than 15° C., and preferably $T_p-T_o$ is less than 10° C.

Preferred SCC polymers formed from the reaction medium used in this invention comprises:

(i) 50 to 100%, preferably 65 to 95%, of units derived from a first hydrophobic monomer selected from the group consisting of alkyl acrylates, alkyl methacrylates, alkyl acrylamides, alkyl methacrylamides, alkyl vinyl ethers and alkyl vinyl esters in which the alkyl groups are n-alkyl groups containing 12 to 50 carbon atoms;

(ii) preferably no more than 35% by weight of units derived from a second hydrophobic monomer selected from the group consisting of alkyl acrylates, alkyl methacrylates, N-alkyl acrylamides, alkyl vinyl ethers, and alkyl vinyl esters in which the alkyl groups are n-alkyl groups containing 4 to 12 carbon atoms; and (iii) at least 2%, and preferably no more than 10% by weight of units derived from at least one hydrophilic monomer selected from the group consisting of acrylic acid, methacrylic acid, 2-acrylamido-2-methylpropane sulfonic acid, hydroxyethyl (meth)acrylate, itaconic acid, acrylamide, methacrylamide, acrylonitrile, methacrylonitrile, tetraalkylammonium acrylates, vinyl acetate and N-vinyl pyrrolidone.

The formed latex compositions have a specific particle size distribution with the mean volume diameter of the particles in the range of 0.1 to 0.5 microns, preferably in the range of 0.25 to 0.35 microns, by the light scattering technique. Small particles are desirable to avoid clogging of spray nozzles when the latex is applied by spraying. In addition, latices formed of large particles tend to be more unstable than latices of small particles. The dispersion mean particle size can be increased by adding increasing amounts of a base such as sodium bicarbonate. Preferably the reaction mixture contains sufficient surfactant and cosolvent that the latex product has a solids content of at least 20%, and more preferably at least 30%, and most preferably at least 35%, based on the weight of the particles.

Core/Shell Products

The crystalline polymers prepared according to the method described above comprises single crystalline phase particles, wherein the monomers used to make the polymer are substantially randomly dispersed within the polymer as a result of use of appropriate amounts of surfactant and comonomer.

In some applications it can be desirable in a first stage to first polymerize the hydrophobic component thereby forming a crystalline copolymer or homopolymer, and then polymerizing the hydrophilic component in a second stage. This results in phase separated particles having a core of predominantly (at least 50% by weight) crystalline polymer and a shell around the core, the shell being formed predominantly of non-crystalline polymer. Thus the particles have two phases. Generally, the core is substantially all crystalline polymer as a first phase, and the shell is substantially all non-crystalline polymer as the shell. This is desirable when there is a need to change the properties of the crystalline polymer, such as tack, without changing the $T_m$. The monomers used to form the shell are not limited to hydrophilic materials, but can also be monomers such as styrene, butyl methacrylate, and the like.

For a core/shell product $T_m$ is substantially the same as the crystalline homopolymer formed from the first hydrophobic monomer. Contrarily, when a second hydrophobic monomer is used and the monomers used to make the polymer are substantially randomly dispersed, the $T_m$ of the formed crystalline polymer is at least 5° C. less than the $T_m$ of the crystalline homopolymer.

Organism Coatings

In the present invention, organisms such as seeds are coated with the latices described above. The composition can be applied to seeds or other organisms of the invention by one or more means known to those skilled in the art. For example, the polymers can be applied by the slurry method, pan coating, or by a continuous spraying and drying process. These procedures can be used to provide one or more layers of coating, which coatings separate an inside environment containing the seed or other organism from the outside environment. The latices are typically applied by spray coating, then the water is evaporated continuously or simultaneously, either by heating or under ambient conditions. The coating formed is non-phytotoxic, at least to the organism coated.

The composition used to form the coating contains sufficient particles that the particulate coating is impermeable to water at a temperature below $T_m$ for extending the dormancy of the organism due to lack of water. However, the water permeability of the coating is at least two times above $T_m$ as compared with the water permeability below $T_m$ so the organism can become non-dormant.

For example, with corn seeds, the coating prevents the seed from imbibing more than 15% by weight of water at temperatures below the seed's minimum germination temperature when the seed is exposed to water over a period of 48 hours. The coating allows the seed to imbibe 25% or more by weight of water in a 48 hour period when the seed is subjected to a temperature above the minimum generation temperature of the seeds. Preferably the coating prevents the seed from imbibing more than 10% by weight of water over a 48 hour period at a temperature below the optimum germination temperature.

Other seed types may have significantly different moisture requirements for germination compared to that of corn. Consequently coatings with different water permeability characteristics from those described above can also be prepared.

Although the present invention is directed principally to coating seeds for controlling the dormancy of the seed, the invention is useful for a wide variety of organisms, and a wide variety of purposes. For example, it can be used for protecting the various organisms from the environment, such as fungi and insects. Among the organisms the coating can be used for are nematodes, bacteria, embryos, eggs, sprouts, bugs, rhizobium, seedlings, potato cuttings and seeds. Among the seeds for which the invention is useful are vegetable seeds, grain seeds, and others. For example, the invention can be used for seeds for canola, maize, cotton, soybean, sugar beets, beans, tomato, potato, tobacco, corn, rice, wheat, sunflower, the brassica family, the solanaceae family, sorghum, barley, lentils, melons, cucumbers, cabbage, brussels sprouts, beans, and peas.

The composition applied to the organism can contain seed coating additives. Exemplary seed coating additives are selected from the group consisting of colorants, fillers, soil pH adjusters, nutrients, seed protectors, phytotoxicity inhibitors, herbicides, growth regulators, soil improvers, fungicides, insecticides, growth stimulants, plant hormones, fertilizers, bird repellents, stimulants to accelerate growth, and innoculants. The coating can contain more than one seed coating additive. Although these additives are referred to herein as "seed coating additive," it is clear that they can be applied to any of the organisms for which the present invention can be used.

Although the seed coating additive can be included as part of the coating, it can also be applied to the organism underneath the coating, i.e., insecticide can be applied to the seed and then the coating can be formed on the seed. Similarly, the additive can be applied after the coating is applied, i.e., on top of the coating. For example, if the additive is a fungicide which is phytotoxic to a seed, by first putting a coating on the seed, and then applying the fungicide, the seed is protected from the adverse effects of the fungicide until germination.

Exemplary fungicides are those given in *List of Phytopharmaceutical Products,* published by the Ministry of Agriculture, Plant, Production Department, Brussels, 1968 and 1981, and in the *Phytosanitary Index* published by the ACTA, Paris, 1981, pages 195–268. Methoxyethyl mercury acetate benomyl, captan, copper hydroxyquinolate, thiram, thiabendazole, ethirmol, maneb and captafol are known fungicides.

Exemplary colorants include compounds such as powdered clay (montmorillonite), and dyes, such as Rhodamine B500, Methyl Violet, Blue 2313, Eosine Y, Sunset Yellow, Magenta, Blue 23123, Pigment Green 7, Tartrazine, Malachite Green, Auramine 0, Oil Yellow 21756, Green 19102 and Methylene Blue 2B, and from titanium dioxide-coated micas (lustres) such as 100 Silver Pearl, 120 Lustre Pearl, 235 Green Pearl, 300 Gold Pearl, 500 Bronze Pearl and 504 Red Pearl.

Among the known soil pH adjustors are calcium carbonate. Representative nutrients are chelates of iron, zinc, manganese, gypsum, metal silicates, elemental sulfur, and vermiculite. Known seed protectors include activated carbon to protect the seed against potentially harmful chemicals such as previously applied pesticides.

Commonly used soil improvers include peat, coffee grounds, and nut shells.

Among commonly used fungicides are carboxin and thiram. Inocculants can include a nitrogen-fixing bacteria.

These seed coating additives are used in an effective amount, typically individually at a level from about 0.01% to about 10%, and preferably from about 0.05% to about 5% by weight of the composition.

The pH of the seed coating composition is typically from about 4 to about 10, and preferably from about 6 to about 9.

A technique for improving the removability of the crystalline polymer with water is to form the polymer with one or more monomers containing free carboxyl groups, wherein at least 50% of the carboxyl groups are neutralized with a neutralizing agent. A suitable neutralizing agent is sodium bicarbonate.

In some applications, it is desirable that the crystalline polymer be formed of a crosslinkable monomer, as described above. This results in the coating on the seeds being shed upon water exposure. For the same purpose, the crystalline monomers can be formed of one or more amphoteric monomers in an amount at least 0.5% by weight of the polymer to enhance removal of the particles from the seed with water. Another technique for improving the removability of the crystalline polymer with water is to form the polymer with one or more monomers containing free carboxyl groups, wherein at least 75% of the carboxyl groups are neutralized with a neutralizing agent. A suitable neutralizing agent is sodium bicarbonate.

The FIGURE shows a coating 10 prepared according to the present invention on a seed 12, the coating being formed in accordance with the present invention, wherein a crosslinking monomer is included in the monomer component. As can be seen, the coating is formed of individual particles 14.

When the seed coating compositions of the present invention are applied, they are applied in an effective amount for coating the seeds. By "effective amount" there is meant amount sufficient to provide the seeds with the benefits desired.

The seed coatings are designed so as to prevent imbibition during conditions unfavorable to germination, but to allow imbibition during conditions most favorable to germination. For each specific type and variety of seed there is a minimum, optimum, and maximum temperature for germination. These temperatures can be determined by those skilled in the art. Information on germination temperature of some common vegetable crops is provided in Plant Propagation: Principles and Practice, 1959, H. T. Hartman and D. E. Kester (Prentice-Hall Publications).

An important advantage of the present invention is the ability to coat a seed so that it (and other coated seeds planted at the same time) begin germination only when the temperature is above the minimum and preferably at the optimum temperature for germination. In general, favorable conditions for the germination of seeds include a temperature in the range of just above 0° C. to about 40° C., more preferably 10° C. to 35° C. By the term "just above 0° C." is meant a temperature at which (at atmospheric pressure) water will be liquid. However, germination can begin if the seed is subjected to large amounts of moisture at temperatures below the optimum germination temperature. Accordingly, the polymeric coatings provided on the coated seeds of the invention are designed so as to prevent imbibition at temperatures below the optimum temperature for germination, but which allow imbibition and thus germination at temperatures at or above the optimum temperature for germination.

Dry seeds such as dry soybean seeds typically contain about 7% to 14% by weight of moisture in their dormant state. If the seed imbibes substantial amounts of water at cooler temperatures, the seed is likely to undergo what is referred to as "imbibitional chilling injury." Such injury can generally be avoided if the seed can be prevented from imbibing no more than from about 17 to about 24% by weight of water over a 48 hour period at low temperatures. Accordingly, the coated seeds of the present invention are preferably provided with coatings which are, at lower temperatures, substantial impermeable to water, or at least do not allow the seed to imbibe more than about 24%, more preferably no more than about 17% by weight of water over a 48 hour period during which it is subjected to moisture and a temperature below the minimum temperature for germination.

It is clear that the coated seeds of the invention must allow imbibition at some point or the seeds will not germinate. Typically, a seed such as a soybean requires a total water content of greater than about 60% by weight in order to undergo optimum germination. Accordingly, the coated seeds of the present invention will preferably allow the seed to imbibe 60% by weight of water over a 48 hour period when the temperature is favorable to the germination of the seed. If imbibition begins at higher temperatures and then the temperatures get cooler, the polymers can reverse their water permeability and halt further imbibition.

Coated seeds of the invention can be designed such that germination takes place at different temperatures and thus at different times, e.g., several centigrade degrees and days apart. This results in the crops maturing at different times. This allows the farmer to make more efficient use of the equipment and/or labor resources. In accordance with yet another embodiment, the germination of male and female plants can be timed so that they occur at times which facilitate or prevent fertilization, depending on the result desired.

The variability in the rate of individual seed germination is small at optimal temperatures and correspondingly great at suboptimal temperatures. This means that the emergence and growth of seeds germinated at suboptimal temperatures is subject to great variability—for example, oats at 7° C. germinate at times varying from 6 to 15 days (90% germination), while oats at 15° C. achieve 90% germination between 4 and 6 days, a spread of only 2 days.

Coated seeds of the invention can be designed such that the coating temperature is set to correlate with that point in the distribution of soil temperature versus seed percent germination per day such that the maximum percent germination occurs in the shortest time period. This results in crops that have a uniform stand throughout their growing cycle and which can be harvested over a shorter time than by allowing conventional (or natural) germination to occur. This benefits the farmer by allowing the farmer to harvest his crop with fewer trips across the field, and to plan the timing of his harvest to fit the farmer's equipment and processing needs.

The polymers of the latex particles are temperature-responsive and are designed and formulated so as to provide a material which is dynamic in nature, that is, changing depending upon the temperature to which it is exposed. The polymeric materials are designed so that they are substantially impermeable to a given material such as oxygen, carbon dioxide or water at a temperature below a given phase transition point and highly permeable to the material at a temperature above the transition temperature. Polymers of the invention are relatively hydrophobic and take up less than 5% of water by weight. They have a first order transition temperature of 40° C. or less and have permeabilities two to three or more times greater at a temperature at or above the transition temperature than below that temperature.

Polymers used in making coated organisms of the invention have a first-order transition temperature or melting point $T_m$ in the range of from just above 0° C. to 40° C. in most cases, but at or below the optimal germination temperature when used with seed. It is preferred that the melting occur rapidly, i.e., over a relatively narrow temperature range, less than about 10° C., preferably less than about 5° C.

The coating is substantially nonpermeable up until the transition temperature is reached, and becomes permeable upon reaching that temperature. The melting "point" of the polymers as described herein is taken as the endotherm peak temperature when measured at a rate of 10° C./min as measured on a differential scanning calorimeter.

EXAMPLES

These and other features, aspects and advantages of the present invention will become better understood from the following examples.

Seed Coatings

The following examples 1–26 relate to seed coatings. The following abbreviations are used in Examples 1–26: C6A, hexyl acrylate (amorphous hydrophobic monomer); C12A, dodecyl acrylate (crystalline hydrophobic monomer); C14A, tetradecyl acrylate (crystalline hydrophobic monomer); C16A, hexadecyl acrylate (crystalline hydrophobic monomer); C18A, octadecyl acrylate (crystalline hydrophobic monomer); C6DA, 1,6-hexanediol diacrylate (crosslinking monomer); CD14A, 1,14-tetradecadiol diacrylate (crosslinking monomer); AA, acrylic acid (hydrophilic monomer); MA, methacrylic acid (hydrophilic monomer); C12SH, dodecyl mercaptan (chain transfer agent); TTT, 1,3,5-triallyl triazine trione (crosslinker); BDE, 1,4-butanediol divinyl ether (crosslinker); TETA, triethylene tetramine (external crosslinker); AH, 10% aqueous ammonium hydroxide available from Baxter; CC, calcium carbonate under the trade name Albaglos, 0.6 microns, available from Specialty Minerals; Zinplex 15 is available from Rohm and Haas (external crosslinker); DEAPA, N, N-Diethyl aminopropylamine is available from Aldrich (external crosslinker); Colloid 211 is a water soluble polyacrylate polymer obtained from Rhone-Poulenc that acts as a dispersant for the calcium carbonate; Defoamer 2010 is available from Dow Corning and is a low surface energy silicone polymer, and Seedmate seed colorant is a product of Loveland Industries Inc.

SP, sodium persulfate (initiator); PP, potassium persulfate (initiator); SBC, sodium bicarbonate (buffer); EAC, ethyl acetate (cosolvent); IPA, isopropanol (cosolvent); NP, n-propanol (cosolvent).

The following are surfactants: SDS, sodium dodecyl sulfate; 15-S-7, 15-S-9 and 15-S-40 are $C_{11}$–$C_{15}$ secondary alcohol ethoxylates which are available from Union Carbide under the trade name Tergitol 15-S-7, 15-S-9 and 15-S-40, respectively; Lodyne S-106A, a fluorosurfactant available from Ciba-Geigy; P1059, an amine salt of dodecyl benzene sulfonic acid which is available from Witco under the trade name Witconate P1059; EMC, sodium dioctyl sulfosuccinate which is available from Witco under the trade name EMCOL DOSS; SLS-R which is a 30% by weight lauryl sulfate solution in water available from Lonza, Inc under the trade name Carsonol SLS-R, and A-102 which is a disodium ethoxylated alcohol half ester of sulfosuccinic acid available from Cytec under the trade name AEROSOL A-102.

Examples 1–6

Preparation of Polymer Latex

A polymer latex for Example 25 was prepared by mixing together C16A (68 g), C6A (27 g), MA (5 g), C4DA (1 g), water (160 g), IPA (40 g), A-102 (2 g), SLS-R (2 g), 15-S-7 (2 g), 15-S-40 (0.5 g), and SBC (0.4 g) in a bottle. The bottle was purged with $N_2$ for 30 min. The bottle was then capped and heated to 70° C., and then PP (0.4 g) was added. The reaction was carried out at 70° C. for 4 h. The reaction exothermed rapidly and a blue latex was formed. The latex was cooled and neutralized with aqueous ammonia.

The latices of Examples 2, 3, and 4 were prepared in the same way described for Example 1 with the same ingredients and amounts as in 1, except that TTT and BDE were substituted for C4DA in Examples 2 and 3, respectively. Example 4 was prepared in the absence of an internal crosslinker.

In Example 29 an internally crosslinked polymer was prepared, where the crosslinking component was 1,4 butanediol diacrylate. The monomers were mixed together: C16A (68 g), C6A (27 g), MA (5 g), 1,4-butanediol diacrylate (1 g). An aqueous phase was prepared with water (160 g), isopropanol (40 g), Aerosol A-102 (4 g), Carsonol SLS-R (2 g), Tergitol 15-S-7 (2 g), Tergitol 15-S-40 (0.5 g), $NaHCO_3$ (0.4 g), and potassium persulfate (0.4 g). The reagents were mixed together and purged with $N_2$ for 30 minutes in a bottle. The bottle was then capped and heated to 70° C., and 0.4 g of potassium persulfate was added. The reaction was carried out at 70° C. for 4 hours. The reaction exothermed rapidly and a blue latex was formed. The latex was cooled and neutralized with aqueous ammonia.

For Example 6 a polymer was prepared with 2-acrylamido-2-methylpropane sulfonic acid (AMPS). C16A (31.5 g), AMPS (6 g of a 50% aq. solution), water (80 g), isopropanol (20 g), Aerosol A-102 (2 g), Carsonol SLS-R (1 g) were mixed together in a bottle and purged with $N_2$ for 20 min. The bottle was then capped and heated to 80° C., and 0.4 g of potassium persulfate was added. The reaction was carried out at 80° C. for 3 h. A bluish tan emulsion was formed, cooled overnight and neutralized with ammonium hydroxide.

Example 7

Preparation of Seed Coating Formulations

Seed coating formulations were prepared that contained:

Type I. Polymer latex containing no internal or external crosslinker (using the latex of Example 4);

Type II. Polymer latex with internal crosslinks (using the latex of Example 1);

Type III. Polymer latex prepared with an external crosslinker (using the latex of Example 4 in the presence of $Zn^{2+}$); and Type IV. Polymer latex with internal and external crosslinks (using the latex of Example 1 in the presence of TETA).

The following procedure was followed to prepare formulations of Type I and II:

A wet grind was prepared consisting of Colloid 211 (1 g), water (20 g), AH (10 g), polymer latex (100 g), and CC (120 g). The wet grind was prepared in a Cowels mixer at 3000 rpm for 30 min (shear rate 126 sec$^{-1}$). The let down was prepared by mixing (VIRTIS Shear mixing at 2000 rpm for 10 min) and consisted of wet grind (125 g), polymer latex (550 g), water (1200 g), and seed colorant (5 g). AH (10 g) was added to the formulation preparations. The let down was used directly to coat the seeds.

For Type III formulations, external crosslinker was added to the let down prior to coating. For example, Zinplex 15 (2.3 g) was added to the type I formulation during the let down (970 g) to form a coating solution. Type III formulations were prepared as follows:

CC (40 g) and water (100 g) were sheared in a VIRTIS at 2000 rpm, and Colloid 211 (0.5 g) mixed with 3 ml water was slowly added and sheared for 2 min. The latex (400 g equivalent to 120 g polymer) was made basic with 10% AH, 4–5 ml and was slowly added followed by the Zinplex and DEAPA (both diluted with 2–3 ml of water) and sheared for about 5 min. Water (500 g) and red dye (3 ml) were added. The coating solution was then filtered through a 63 micron mesh filter. Towards the end of the filtration 2 drops of defoamer were added.

For Type IV formulations, external crosslinker was added to the let-down during its preparation. For example, TTM (2.4 g) was added to the type II formulation let down (940 g) or Zinplex (8.6 g) was diluted with 20 g water and added to the type II formulation let down (1895 g). Type IV formulations were prepared as follows:

A wet grind was prepared form Colloid 211 (2 g), water (20 g), aqueous AH (20 g), latex (250 g) and CC (360 g). The grind was mixed by blending in a Cowels mixer at 3000 rpm for 30 min. A concentrate preparation was made from wet grind (650 g), latex (2150 g), Zinplex 15 (18.4 g), and Seedmate Colorant (25 g). The coating solution was prepared by diluting the concentrate (540 g) with water (880 g).

All of these formulations have a $T_m$ of about 19–21° C.

Examples 8–20

Seed Testing

Seed Coating Procedure

Seeds were coated with the formulations of Example 7 using seed coating equipment for water based coatings manufactured by Diamond Coating Equipment (Tucson, Arizona). The seed coating equipment consisted of a perforated pan fitted with baffles, and capable of handling about 20 lbs of seed/batch. The seeds were coated with a fine spray of the formulation from a spray nozzle located in the coating pan. To assist in drying of the seeds the coater was equipped with a hot air inlet and an air exhaust.

An exemplary coating procedure involving soybeans utilized Soybeans (6 kg), which were loaded into the seed coating equipment. The coating formulation was pumped to the spray nozzle using a peristaltic pump. The pan was rotated at a rate of 12–13 rpm to keep the seeds thoroughly mixed. The coating was started by turning the spray nozzle on pneumatically, and pumping at a rate of 30 ml/min. The pan temperature was maintained at 30° C. and the coating was carried out for 17 min. The spray nozzle was shut off, the pan rotation stopped, and the coated seeds were removed.

Seed Testing

Seeds were tested for water uptake and germination/plant emergence as a function of temperature under controlled conditions. The testing methods used are similar to those prescribed by the Association of Seed Analysts (AOSA) testing methods, and Rules of Testing Seeds (Association of Official Seed Analysts. Journal of Seed Technology, Vol 12, No: 3, 1988). The performance of the coated soybean seeds were measured by the water uptake of the seeds at two temperatures at 10 and 25° C. at 48 h, and the germination of the seeds at 25° C. for 7 days, and at 10° C. for 7 days followed by 7 days at 25° C. Table 2 gives the water uptake of representative coatings along with the water uptake of the uncoated seed (Example 8) used as a control.

Paper Towel Germination Test

Germination paper sheets(Anchor #38 and #76 seed germination paper (10"×15")) were allowed to equilibrate for about 30 min with approximately two times their dry weight of water.

Two moistened sheets were placed on the benchtop, and 10 g of seeds were placed along the length of the paper, about a third of the length from the top. Another wet sheet of paper was placed on top. A hem about 1" wide at the bottom was folded and the sheets rolled, and set vertically. Four to five such paper dolls were secured loosely with a pair of rubber bands and were placed vertically in a plastic bag and placed in incubators maintained at 10° C. and 25° C., respectively. After the specified amount of time (48 hours), the seeds were removed and weighed.

TABLE 1

| Example | Type | Polymer Latex | Coating Type | % Water Uptake at 10° C. | % Water Uptake at 25° C. |
| --- | --- | --- | --- | --- | --- |
| 34 | Control | No coating | No coating | 102 | 120 |
| 35 | II | C16A/C6A/AA/C14DA (68/27/5/1) | Internal X-linker | 11 | 80 |

TABLE 1-continued

| Example | Type | Polymer Latex | Coating Type | % Water Uptake at 10° C. | % Water Uptake at 25° C. |
|---|---|---|---|---|---|
| 36 | IV | C16A/C6A/AA/C14DA (68/27/5/1) | Int, and 0.5% Zn External | 13 | 92 |
| 37 | IV | C16A/C6A/AA/C14DA (68/27/5/1) | Int, and 2% TETA Ext | 20 | 99 |
| 38 | IV | C16A/C6A/AA/C14DA (68/27/5/1.5) | Int, 1% Zn Ext | 18 | 82 |
| 39 | IV | C16A/C6A/AA/C14DA (68/27/5/1.5) | Int, 1.5% Zn Ext | 30 | 92 |
| 40 | IV | C16A/C6A/MA/C14DA (68/27/5/1) | Int, 0.5% Zn Ext | 25 | 84 |
| 41 | II | C16A/C6A/MA/C14DA (68/27/5/1) | Int, no Ext | 15 | 68 |
| 42 | IV | C16A/C6A/AA/C14DA (68/27/3/1) | Int, 0.5% Zn Ext | 27 | 93 |
| 43 | III | C16A/C6A/AA (68/27/7.5) | No Int., 0.5% Zn Ext | 36 | 97 |
| 44 | II | C16A/C6A/AA/C4DA (68/27/5/1) | Int, No Ext | 20 | 96 |
| 45 | I | C16A/C6A/MA/68/27/7.5 | No Int, No Ext | 36 | 48 |
| 46 | III | C16A/C6A/MA/68/27/7.5 | No Int, 0.5% Zn Ext | 36 | 40 |

As illustrated in the Table 1 the presence of an internal crosslinker (types II and IV) decreased the amount of water uptake at low temperatures (10° C.) and increased the water uptake at higher temperatures (25° C.) because the seed coating fell apart more easily once the seeds started expanding. The presence of an external crosslinker improved the mechanical stability of the seed coating. Thus a combination of external and internal crosslinkers can be employed to select the water permeabilities of water coatings at various temperatures.

Example 21

Corn Coating

This example demonstrates coating of hybrid corn. A wet grind consisting of Colloid 211 (0.4 g), ammonia (0.2 g, 50/50 v/v), water (190 g) and $CaCO_3$ (330 g) was blended in a Cowels mixer at 3000 rpm for 30 min. The wet grind (172 g) was mixed with the polymer latex of Example 7(C16A/C6A/MA/C6DA, 70/25/5/0.5) (705 g) ($T_m$ of 20 to 21° C.) in a VIRTIS mixer. Zinplex 15 (5.4 g diluted with 20 g water) was added slowly into the formulation followed by Lodyne S-106A (2.5 g diluted with 20 g water). Seed colorant (8 g), and water (540 g) were added to complete the formulation. The coating solution was filtered through a 60 micron wire mesh filter. Hybrid Corn (4 kg) was loaded into the seed coater, and the coating was carried out at a flow rate of 60 mL/min for a period of 11 min. The internal temperature of the pan was kept at ° 40° C.

Example 22

Rice Coating

This example demonstrates coating of rice. A wet grind was prepared by mixing in a Cowels mixer Colloid 211 (2 g), ammonium hydroxide (40 g of 10% aq. solution), the polymer latex C16A/C6A/MA/C6DA (70/25/5/0.5)) (250 g) ($T_m$ of 20 to 21° C.), and $CaCO_3$ (360 g) for 30 min at 3000 rpm. The concentrate was prepared from the wet grind by mixing the wet grind with the polymer latex (2150 g), and 20 g of 10% aq. ammonia. The coating solution was prepared by combining under light shear the concentrate (550 g), water (850 g), Zinplex 15 (3.6 g with 20 g water), and the seed colorant (10 g). Three kg of seeds were coated at a flow rate of 40 mL/min for 30 min. The pan temperature was maintained at 30° C.

Example 23

Wheat Coating

The formulation of Example 22 was used for coating wheat. The coating was carried out at 40 mL/min for a period of 20 min, with a pan temperature of 35° C.

Example 24

Sugarbeet Coating

This example demonstrates coating of sugarbeets. The polymer latex of Example 8(C14A/C6A/MA/C6DA (80/15/5/0.7)) with a lower $T_m$ (12° C.) was used in the coating of sugarbeets. All other components of the formulation were identical to those described for Example 22. Sugarbeets (4 kg) were coated at a spray rate of 30 mL/min, and a pan temperature of 30° C. were coated for 40 min.

Example 25

Cottonseed Coating

This example demonstrates coating of cottonseeds. A wet grind was prepared by blending Colloid 211 (2 g), ammonia (40 g, 10% aq. solution), latex (250 g) (C16A/C6A/AA/C14DA (70/25/8/1)), and $CaCO_3$ (360 g). A concentrate was prepared by mixing the wet grind with the polymer latex (2150 g) in a VIRTIS mixer, followed by 18.4 g. The cottonseeds (4 kg) were coated at a flow rate of 30 mL/min for 45 min with the pan temperature not exceeding 30° C.

Coatings on other seed varieties, including lentils, chickpeas and sweet corn, were prepared using similar formulations as described above.

Example 26

Corn Coating Test

Two hybrid corn varieties from Sucrosco Seeds (Manilla, Iowa) were field tested. They were planted in Casey, Iowa.

Prior to planting some of the seeds were left uncoated, other were coated with (C16A/C6A/MA/C6DA (70/25/5/0.5), 1% Zinplex) (Example 26A) or (C16A/C6A/MA/C6DA (70/25/5/0.5), 0.5% Zinplex) (Example 26B). Seed were planted at different times (Mar. 23, 1996, Apr. 3, 1996, and Apr. 17, 1996) and stand counts were performed 3 weeks after planting. The results are shown in Table 2 and are the average of four different experiments.

TABLE 2

| Planting Date | Hybrid Corn Variety | Uncoated (stand count) | Example 26A Coating (stand count) | Example 26B Coating (stand count) |
|---|---|---|---|---|
| 3/23/96 | A | 1.8 | 19 | 51 |
| 3/23/96 | B | 23 | 44 | 69 |
| 4/3/96 | A | 74 | 91 | 102 |
| 4/3/96 | B | 110 | 111 | 114 |
| 4/17/96 | A | 106 | 115 | 104 |
| 4/17/96 | B | 110 | 119 | 121 |

As can be seen from Table 2, coating the seeds with the polymer latex coatings protect the seeds when the seeds are planted early in the planting season when there is a possibility for the seeds to suffer chilling injury. When seeds are planted later in the planting season, i.e., when it is unlikely for the soil temperature to go below 0° C., the seed coating does not have an adverse effect on corn germination because the seed coating is readily released if the temperature remains above the $T_m$ of the seed coating polymer and the seed starts expanding.

The reader's attention is directed to all papers and documents, if any, which are filed concurrently with this specification and which are open to public inspection with this specification, and the contents of all such papers and documents are incorporated herein by reference.

All the features disclosed in this specification (including any accompanying claims, abstract and drawings), and/or all of the steps or any method or process so disclosed, may be combined in any combination, except combinations where at least some of such features and/or steps are mutually exclusive.

Each feature disclosed in this specification (including any accompanying claims, abstract, and drawings), may be replaced by alternative features serving the same, equivalent or similar purpose, unless expressly stated otherwise. Thus, unless expressly stated otherwise, each feature disclosed is one example only of a generic series of equivalent or similar features.

Although the present invention has been described in considerable detail with reference to certain preferred versions thereof, other versions are possible. Therefore, the scope of the appended claims should not be limited to the description of the preferred versions contained herein.

What is claimed is:

1. A method for extending the dormancy of a seed comprising step of applying to the seed an aqueous, non-phytotoxic composition comprising (i) water; and (ii) particles suspended in the water, the particles comprising a crystalline polymer having a melting temperature, $T_m$, greater than 0° C. and less than about 40° C., wherein a particulate coating forms on the seed by water evaporating from the composition, wherein the composition containing sufficient particles that the particulate coating is impermeable to water at a temperature below $T_m$ for extending the dormancy of the organism due to lack of water, and wherein the water permeability of the coating is at least two times more above $T_m$ as compared with the water permeability below $T_m$ so that the organism can become non-dormant.

2. A method for controlling the dormancy of a seed comprising the step of applying to the seed an aqueous, non-phytotoxic composition comprising:

a) water; and b) particles suspended in the water, the particles comprising the crystalline, polymeric, cross-linked reaction product of a monomer component comprising:

(1) a hydrophobic monomer component comprising a first hydrophobic monomer such that a homopolymer thereof is crystallizable, (2) a hydrophilic monomer component comprising a hydrophilic monomer, the weight ratio of the hydrophobic monomer component to the hydrophilic monomer component being sufficiently large that the polymeric reaction product is crystallizable, and (3) sufficient crosslinking monomer having at least two polymerizable groups that the polymeric reaction product has a gel content of at least 50%; and c) sufficient surfactant to suspend the particles in the water, wherein the monomer content of the latex is less than 1% by weight based on the weight of the particles, and the crystalline polymer has a melting temperature, $T_m$, greater than 0° C. and less than about 40° C., the composition containing sufficient particles that drying the composition forms a coating, wherein a particulate coating forms on the seed by water evaporating from the composition.

3. A composition suitable for coating a seed for controlling the dormancy of the seed, the composition being non-phytotoxic to the seed and comprising:

a) water;

b) particles suspended in the water, the particles comprising a crystalline polymer having a melting temperature $T_m$ of from about 0 to about 40° C.; and c) a seed coating additive.

4. A composition suitable for coating a seed for controlling the dormancy of the seed, the composition being non-phytotoxic and comprising:

a) water;

b) particles suspended in the water, the particles comprising a crystalline polymer having a $T_m$ of from about 0 to about 40° C.;

c) a seed coating additive; and d) a surfactant.

5. The method of claim 1 including the additional step of heating the applied composition for evaporating water therefrom.

6. The method of claim 1 wherein the composition comprises a seed coating additive.

7. The method of claim 2 wherein the composition comprises a seed coating additive.

8. The composition of claim 4 wherein the seed coating additive is selected from the group consisting of colorants, fillers, pH adjusters, nutrients, seed protectors, phytotoxicity inhibitors, herbicides, growth regulators, soil improvers, fungicides, insecticides, growth stimulants, plant hormones, fertilizers, bird repellents, and innoculants.

9. The composition of claim 4 wherein the organism is corn seeds.

10. The invention of claim 1 or 3 wherein the particles comprise the crystalline, polymeric, crosslinked reaction product of a monomer component comprising:

(1) a hydrophobic monomer component comprising a first hydrophobic monomer such that a homopolymer thereof is crystalline, (2) a hydrophilic monomer component comprising a hydrophilic monomer, the weight ratio of the hydrophobic monomer component to the hydrophilic monomer component being sufficiently large that the polymeric reaction product is crystalline, and (3) crosslinking monomer having at least two polymerizable groups in a quantity sufficient that the polymeric reaction product has a gel content of at least 50%.

11. The invention of claim 10 wherein the weight ratio of the hydrophobic monomer component to the hydrophilic monomer component is from about 10:1 to about 50:1.

12. The invention of claim 2 wherein the weight ratio of the hydrophobic monomer component to the hydrophilic monomer component is from about 10:1 to about 50:1.

13. The invention of claim 1, 2, or 3 wherein the average particle size of the particles is less than 1 micron.

14. The invention of claim 10 wherein the homopolymer of the first hydrophobic monomer has a melting temperature $T_m$, and wherein the hydrophobic monomer component comprises a second hydrophobic monomer having a glass transition temperature $T_g$ which is less than $T_m$, wherein a homopolymer of the second hydrophobic monomer is amorphous, and wherein the monomer component contains a sufficient amount of the second hydrophobic monomer that the polymeric reaction product has a melting temperature at least 5° C. less than $T_m$.

15. The invention of claim 2 wherein the homopolymer of the first hydrophobic monomer has a melting temperature $T_m$, and wherein the hydrophobic monomer component comprises a second hydrophobic monomer having a glass transition temperature $T_g$ which is less than $T_m$, wherein a homopolymer of the second hydrophobic monomer is amorphous, and wherein the monomer component contains a sufficient amount of the second hydrophobic monomer that the polymeric reaction product has a melting temperature at least 5° C. less than $T_m$.

16. The invention of claim 10 wherein the homopolymer of the first hydrophobic monomer has a melting temperature $T_m$, and wherein the hydrophobic monomer component comprises a second hydrophobic monomer having a glass transition temperature $T_g$ which is greater than $T_m$, wherein a homopolymer of the second hydrophobic monomer is amorphous, and wherein the monomer component contains a sufficient amount of the second hydrophobic monomer that a coating formed from the latex has a tack at ($T_m$+10° C.) less than 50% of the tack at ($T_m$+10° C.) of a coating formed from the same latex without the second hydrophobic monomer.

17. The invention of claim 2 wherein the homopolymer of the first hydrophobic monomer has a melting temperature $T_m$, and wherein the hydrophobic monomer component comprises a second hydrophobic monomer having a glass transition temperature $T_g$ which is greater than $T_m$, wherein a homopolymer of the second hydrophobic monomer is amorphous, and wherein the monomer component contains a sufficient amount of the second hydrophobic monomer that a coating formed from the latex has a tack at ($T_m$+10° C.) less than 50% of the tack at ($T_m$+10° C.) of a coating formed from the same latex without the second hydrophobic monomer.

18. The invention of claim 16 wherein the weight ratio of the first hydrophobic monomer to the second hydrophobic monomer is at least 1:1.

19. The invention of claim 17 wherein the weight ratio of the first hydrophobic monomer to the second hydrophobic monomer is at least 1:1.

20. The invention of claim 2 wherein the crystalline polymer has a melting temperature $T_m$ and an onset-of-melting temperature, $T_o$, wherein $T_m$-$T_o$ is less than 10° C.

21. The invention of claim 3 wherein the crystalline polymer is a side chain crystalline polymer.

22. The invention of claim 21 wherein the side chain crystalline polymer is a thermoplastic elastomer.

23. The invention of claim 1 or 3 containing at least 25% by weight particles.

24. The invention of claim 14 wherein the first and second hydrophobic monomers are n-alkyl (meth)acrylates.

25. The invention of claim 15 wherein the first and second hydrophobic monomers are n-alkyl (meth)acrylates.

26. The invention of claim 16 wherein the first and second hydrophobic monomers are n-alkyl (meth)acrylates.

27. The invention of claim 17 wherein the first and second hydrophobic monomers are n-alkyl (meth)acrylates.

28. A seed prepared by the method of claim 1 or 2.

29. The invention of claim 28 wherein the seed is seeds selected from the group consisting of seed for canola, corn, cotton, soybean, sugar beets, beans, tomato, potato, tobacco, rice, wheat, sunflower, the brassica family, the solanaceae family, sorghum, barley, lentils, melons and cucumber.

30. The invention of claim 1 or 2 wherein the coating prevents the seeds from imbibing more than 24% by weight of water at a temperature below the seeds' minimum germination temperature when the seed is exposed to water over a period of 48 hours.

31. The invention of claim 28 wherein the coating prevents the seeds from imbibing more than 24% by weight of water at a temperature below the seeds' minimum germination temperature when the seed is exposed to water over a period of 48 hours.

32. The invention of claim 28 wherein the coating is crosslinked with an external crosslinker.

33. The invention of claim 1 including a seed coating additive in the coating.

34. The invention of claim 1 including the step of applying a seed coating additive to the seed before coating the seed.

35. The invention of claim 1, including the step of applying a seed coating additive to the coated seed.

36. The seed prepared by the method of claim 33, 34, or 35.

* * * * *